United States Patent [19]

Eibeck et al.

[11] 4,371,707
[45] Feb. 1, 1983

[54] PROCESS FOR THE CONVERSION OF BORON TRIFLUORIDE DIMETHYL ETHER COMPLEX TO THE BORON TRIFLUORIDE DIALKYL ETHER COMPLEX

[75] Inventors: Richard E. Eibeck, Orchard Park; Martin A. Robinson, East Amherst; Francis E. Evans; Eugene B. Recla, both of Hamburg, all of N.Y.

[73] Assignee: Allied Corporation, Morris Township, Morris County, N.J.

[21] Appl. No.: 216,045

[22] Filed: Dec. 15, 1980

[51] Int. Cl.³ .............................................. C07F 5/02
[52] U.S. Cl. ..................................................... 568/6
[58] Field of Search ............................................ 568/6

[56] References Cited

U.S. PATENT DOCUMENTS

| 2,751,285 | 6/1956 | Bartleson | 568/6 X |
| 2,796,330 | 6/1957 | Crist et al. | 423/249 |
| 2,834,717 | 5/1958 | Shiah | 568/6 X |
| 2,906,771 | 9/1959 | Girardot et al. | 568/6 X |

OTHER PUBLICATIONS

Steinberg et al., Progress in Boron Chemistry, The MacMillan Co., N.Y. vol. 1 (1964) pp. 112-114.

Trans. Faraday Soc., 59 (489), 1962-1971 (1963), R. A. Craig et al.
Report No. 78.10-1-3 (1953) "The Preparation of Diethyl Ether—Boron Trifluoride Complex" Kenton Atwood.

Primary Examiner—Helen M. S. Sneed
Attorney, Agent, or Firm—Thomas D. Hoffman; Jay P. Friedenson

[57] ABSTRACT

A process for the conversion of boron trifluoride dimethyl ether complex to boron trifluoride dialkyl ether complex substantially free of dimethyl ether impurities, which comprises reacting the boron trifluoride-dimethyl ether complex, in the liquid phase, in the presence of dialkyl ether wherein at least one of the alkyl groups contains at least two carbon atoms, in a restricted vapor equilibration region, while simultaneously sweeping the said vapor equilibration region with a substantially inert gas, and heating to distill off the dimethyl ether. High purity of the boron trifluoride dialkyl ether complex is attained with this method, with only minimal traces of the boron trifluoride dimethyl ether complex, dimethyl ether remaining. The preferred product is boron trifluoride diethyl ether.

11 Claims, No Drawings

PROCESS FOR THE CONVERSION OF BORON TRIFLUORIDE DIMETHYL ETHER COMPLEX TO THE BORON TRIFLUORIDE DIALKYL ETHER COMPLEX

DESCRIPTION

BACKGROUND OF THE INVENTION

The present invention relates to a process for the conversion of boron trifluoride dimethyl ether complex into boron trifluoride dialkyl ether complex, substantially free of boron trifluoride dimethyl ether complex. The present invention more particularly relates to a process for the conversion of boron trifluoride dimethyl ether complex to boron trifluoride diethyl ether complex, substantially free of dimethyl ether impurities.

Boron trifluoride dimethyl ether complex is used in industry to prepare, by means of enrichment and fractionation procedures, a boron trifluoride dimethyl ether complex fraction that is rich in the boron-10 isotope. The boron-10-enriched boron trifluoride dimethyl ether complex fraction is then converted to elemental boron-10 which is subsequently used as a neutron moderator in nuclear applications. In the course of the fractionation process to produce the boron-10-enriched boron trifluoride dimethyl ether complex fraction, approximately 80 percent of the starting reactant boron trifluoride dimethyl ether complex remains as effluent, i.e. a boron-11 isotope-rich, boron-10 isotope-free, boron trifluoride dimethyl ether complex, which is presently decomposed and dissolved. Such boron-10 isotope-free boron trifluoride dimethyl ether complex reactant disposal is expensive, and involves the waste of a potentially valuable source material. Therefore, it is considered commercially significant to reclaim the boron-10-isotope-depleted boron trifluoride dimethyl ether complex by means of its subsequent conversion to the boron trifluoride diethyl ether complex.

The boron trifluoride dialkyl ether complexes, for example boron trifluoride diethyl ether complex, further have important commercial and industrial uses as catalysts in numerous acetylation, alkylation, polymerization, dehydration and condensation reactions. Boron trifluoride diethyl ether complex has been obtained by reacting excess diethyl ether with boron trifluoride dimethyl ether complex. However, the boron trifluoride diethyl ether complex so produced contains residual dimethyl ether, and boron trifluoride dimethyl ether complex.

Accordingly, it is therefore an object of the present invention to provide an economical process for converting the boron trifluoride dimethyl ether complex to the useful boron trifluoride dialkyl ether complex.

It is a further object of the present invention to provide an improved process for the conversion of the boron trifluoride dimethyl ether complex to the boron trifluoride diethyl ether complex, substantially free of dimethyl ether impurities.

These and other objects and advantages of the present invention will become apparent from the following description.

SUMMARY OF THE INVENTION

In accordance with the objects of the present invention there is provided a process for the conversion of boron trifluoride dimethyl ether complex into boron trifluoride dialkyl ether complex substantially free of dimethyl ether impurities, which comprises:

(a) contacting the boron trifluoride dimethyl ether complex substantially free of boron trifluoride, in the liquid phase, with an effective amount of dialkyl ether wherein at least one of the alkyl groups contains at least two carbon atoms, in a reaction zone, to form a liquid reaction mixture comprising boron trifluoride dialkyl ether complex and residual dimethyl ether and excess diethyl ether;

(b) restricting vapor equilibrium region above the liquid reaction mixture in the reaction zone while heating the liquid reaction mixture for a time and at a temperature sufficient to remove the residual dimethyl ether and to form boron trifluoride dialkyl ether complex substantially free of dimethyl ether impurities; and (c) recovering boron trifluoride dialkyl ether complex substantially free of boron trifluoride dimethyl ether complex.

There is further provided a process for the conversion of boron trifluoride dimethyl ether complex into boron trifluoride diethyl ether complex substantially free of dimethyl ether impurities, which comprises:

(a) contacting about one mole of boron trifluoride dimethyl ether complex substantially free of boron trifluoride, in the liquid phase, with about 2 to about 3 moles of diethyl ether, in a reaction zone at a temperature of about $-30°$ C. to about $35°$ C. to form a liquid reaction mixture comprising boron trifluoride diethyl ether complex, residual dimethyl ether, and excess diethyl ether;

(b) restricting vapor equilibrium region above the liquid reaction mixture in the reaction zone, while heating the liquid reaction mixture at a temperature from about $35°$ C. to no more than about $45°$ C. for a time sufficient to remove the residual dimethyl ether and excess diethyl ether and to form boron trifluoride diethyl ether complex substantially free of dimethyl ether impurities, the volume ratio of said vapor region to said liquid reaction mixture being about 0.5:1 to about 0.8:1; and (c) recovering boron trifluoride diethyl ether complex substantially free of dimethyl ether impurities.

The boron trifluoride-dimethyl ether complex reactant may be the waste effluent from the boron-10 fractionation process, as described above.

DETAILED DESCRIPTION OF THE PRESENT INVENTION

The present invention provides a process for production of boron trifluoride dialkyl ether complex substantially free of boron trifluoride dimethyl ether complex. The contacting of boron trifluoride dimethyl ether with dialkyl ether having at least one alkyl group containing at least two carbon atoms produces a liquid reaction mixture containing boron trifluoride dialkyl ether complex, dialkyl ether and residual dimethyl ether. This residual dimethyl ether is very difficult to remove even though the temperature of the liquid reaction mixture containing same is about $35°$ C., a temperature well above the boiling point of dimethyl ether. Surprisingly, it was discovered that by restricting the vapor equilibrium region above the liquid reaction mixture in the reaction zone while heating the liquid reaction mixture, the residual dimethyl ether is removed and there was obtained boron trifluoride dialkyl ether complex containing less than about 2 area % by NMR of dimethyl ether and/or boron trifluoride dimethyl ether complex.

By sweeping the restricted vapor equilibrium region above the liquid reaction mixture with a substantially dry inert gas, the boron trifluoride dialkyl ether complex was found to contain less than about 0.3% dimethyl ether and/or boron trifluoride dimethyl ether complex. Substantially dry nitrogen is the preferred inert gas.

The dialkyl ether used to contact boron trifluoride dimethyl ether complex contains at least one alkyl group having at least two carbon atoms. Dialkyl ethers found useful in the present invention have the formula $R_1R_2O$ wherein $R_1$ is an acyclic alkyl group containing two to six carbon atoms and wherein $R_2$ is an acyclic alkyl group having one to six carbon atoms. Diethyl ether is the preferred dialkyl ether.

The effective amount of dialkyl ether is chosen such that the molar ratio of boron trifluoride dimethyl ether complex to dialkyl ether is in the range of from about 1:1 to about 1:3.5, preferably about 1:2 to about 1:3, most preferably 1:3.

Although a large excess of the reactant dialkyl ether will not deleteriously affect the reaction results, large amounts of reactants will complicate the recovery of boron trifluoride dialkyl ether complex, and require larger equipment which is difficult to maintain substantially dry and entails laborious recycling of recovered dialkyl ether (see Comparative Example 3). Accordingly, it is preferred not to use more than about a 200 percent excess of the diethyl ether reactant, i.e. the 1:3 molar ratio mentioned supra.

The boron trifluoride dimethyl ether complex reactant from various sources is suitable for use in accordance with the process of the present invention, including the boron trifluoride dimethyl ether complex forms which have not been depleted in the boron-10 isotope in the enrichment process as discussed above.

Amines could also be used in place of the dialkyl ethers complexing agents. Acyclic and cyclic aliphatic amines are preferred over aromatic compounds. The base requirements of the process are as follows: (a) the stabilities of the competing complexes should be similar or favoring the complex used for recovering the $BF_3$; (b) the boiling point of the complexing agents should be such that the complexing agent to be removed can be easily fractionated from the desired complexing agent; and (c) the boiling point of the complexing agent to be removed should be significantly lower than the temperature of complete dissociation of the desired complex.

By "essentially free of boron trifluoride" it is intended to convey that the only required initial reactants are the boron trifluoride dimethyl ether complex and the dialkyl ether reactant. This does not exclude nonreactive additives, but is intended to exclude other potential initial reactants such as boron trifluoride. However, once the residual dimethyl ether is removed from the boron trifluoride dialkyl ether complex, boron trifluoride can be added to convert the excess dialkyl ether into boron trifluoride dialkyl ether complex (see Example 9).

By "substantially free of dimethyl ether impurities", it is meant that the boron trifluoride dialkyl ether complex contains less than about 2% to about 1.5% by area, preferably less than about 1 to about 0.9%; more preferably less than about 0.3% of dimethyl ether impurities such as dimethyl ether, boron trifluoride alkylmethyl ether complex and boron trifluoride dimethyl ether complex.

Gaseous by-products are separated from the liquid reaction mixture comprising boron trifluoride dialkyl ether complex by means of conventional fractional distillation procedures. One of the gaseous by-products of the present invention process is dimethyl ether, which has a number of important industriaL commercial uses, including the complexing with boron trifluoride in order to provide the boron trifluoride dimethyl ether complex which is capable of then being enriched for use as described above.

The preferred boron trifluoride diethyl ether complex is also commercially useful as a polymerization catalyst for a variety of chemical reactions, such as the hydrogenation of 1-methylcyclohexene, the oligomerization of (R)-tert-butyloxirane, the reduction of aldehydes and ketones by organosilanes, the reaction of acetylglycols and acetylpseudoglycols with sodium salt, and others.

The process of the present invention is relatively simple, requiring only conventional fractional distillation apparatus, and takes place over a wide range of reaction temperatures, with or without agitation of the reactants.

It was rather surprising to discover that this reaction would proceed in the facile fashion that it does, in view of the fact that it is reported that the boron trifluoride dimethyl ether complex is more stable than the boron trifluoride diethyl ether complex, and other higher homologues. (see *Trans. Faraday Soc.* 59(489) 1962–1971 (1963)).

In development of the present invention, it was found that 85 percent of the boron trifluoride dimethyl ether complex dissociated at 95° C., whereas 92 percent of the boron trifluoride diethyl ether complex dissociated at 95° C. Apparently, the lower boiling point of the dimethyl ether component (−23.7° C.), as compared to that of the diethyl ether component (34.6° C.), permits the dimethyl ether to vaporize off, and the residual boron trifluoride will then complex with the less volatile remaining diethyl ether.

Applicants do not, however, wish to suggest that other theories of the modus operandi of this invention may not be applicable.

Potential competitive contemporary technology would require several steps for separating the boron trifluoride and dimethyl ether found in the complex, and would also require more complicated equipment. As an example, addition of calcium fluoride ($CaF_2$) to the boron trifluoride-dimethyl ether complex would liberate dimethyl ether and form calcium boron tetrafluoride ($Ca(BF_4)_2$). The latter compound would subsequently need to be calcined in order to liberate boron trifluoride for subsequent reuse.

During the course of the reaction of the process of the present invention, the desired end product, boron trifluoride dialkyl ether complex, substantially free of dimethyl ether impurities, is recovered by suitable distillation recovery procedures.

The present invention allows for the recovery of dimethyl ether product quite readily. The recovered dimethyl ether, however, contains significant quantities of dialkyl ether, for example diethyl ether, and, therefore, would have to be purified prior to the use thereof.

The process of the present invention will proceed readily upon contacting the dialkyl ether reactant material with the boron trifluoride dimethyl ether complex starting reactant material at a temperature in the range of from about −20° C. to +20° C., preferably at room temperature, but it is generally preferred to promote contact between the starting materials with agitation, as well as slowly increase the reaction temperature to from about 20° C. to about 35° C.

Since the process of the present invention is carried out in the liquid phase, the reaction temperatures should be such as to maintain the starting reactant materials as liquids. The process reaction will proceed most efficiently at any reaction temperatures at which both starting reactant materials are in the liquid phase. Heat may also optionally be provided to the reaction mixture in order to assist in the separation of the gaseous by-products. In order to allow the dimethyl ether to be removed smoothly it is preferred to maintain the temperature of the starting materials in the range of about −30° to about +35° C., preferably +20° C. to +35° C., during the initial contacting step. The temperature is then raised in the range of from about 35° C. to no more than about 50° C., preferably from about 40° C. to no more than about 45° C. A final reaction temperature of about 40° to about 45° C. should be maintained for at least about one hour. The order of contacting was not found to be critical. Both the normal addition wherein the dialkyl ether was added to the boron trifluoride dimethyl ether complex and the reverse addition wherein the dialkyl ether was always in excess produced boron trifluoride dialkyl ether complex containing less than about 2% by area of boron trifluoride dimethyl ether complex.

It is a preferred feature of the present invention that a vapor equilibrium region above the reaction liquid volume be restricted while the liquid reaction mixture is heated at a temperature in a range of about 35° to no more than about 50° C., preferably from about 35° C. to no more than about 45° C. for a time sufficient to remove dimethyl ether.

It has been determined that the preferred final temperature range in which to carry out the reaction, while restricting the vapor equilibrium region, is from at least about 40° C. to about 45° C. As the final reaction temperature was increased to about 40° C., the "dimethyl ether impurities" content remaining in the boron trifluoride dialkyl ether complex was found to be less than about 2.0, usually 1.5 area percent.

The remaining dimethyl ether impurities content of the product volume, i.e. less than about 2.0 area percent, usually about 1.5 area percent, was found to be very difficult to remove, as the free dimethyl ether appears to have significant solubility in the liquid boron trifluoride diethyl ether complex solution, even at the boiling point. Further, the equilibrium mixture of the two ether complexes, i.e., the boron trifluoride dimethyl ether and the boron trifluoride diethyl ether, where the dimethyl ether is low, appears to be quite stable.

Only when the restricted vapor equilibrium region was essentially eliminated, while heating of the liquid reaction at a temperature in the range of about 35° to no more than about 50° C. was this equilibrium altered, and the remaining dimethyl ether impurities content reduced to an amount less than 1.0 area percent. When the restricted vapor equilibrium region over the liquid reaction mixture, heated to a temperature of about 35° to no more than about 50° C., was swept with an excess of substantially dry inert gas, preferably substantially dry nitrogen, the dimethyl ether impurities content was reduced to an amount less than about 0.3 area percent.

The volume ratio of vapor equilibrium region over the liquid reactant mixture to the liquid reaction mixture was varied from about 0.3:1 to about 3:1, preferably about 0.5:1 to 0.8:1, more preferably about 0.6:1 to about 0.7:1. While it was found convenient to restrict the vapor equilibrium region above the liquid reaction mixture by feeding a maximum charge of reactants, i.e., boron trifluoride dimethyl ether complex and dialkyl ether, to the reaction zone, other methods of restriction, such as a designing reactor to have variable volume, are considered within the scope of the invention.

When the restricted vapor equilibrium region was slowly and continuously swept with an excess of a substantially dry inert gas, such as substantially dry nitrogen, helium, neon, argon, krypton, xenon and substantially dry radion, preferably substantially dry nitrogen, i.e. nitrogen gas containing less than 0.01 weight % of water vapor, or the vapor equilibrium region was reduced even further by means of charging maximum amounts of starting reactants to the reaction flask, significantly reduced quantities of dimethyl ether impurities were found in the boron trifluoride dialkyl ether complex. The substantially dry nitrogen gas sweep preferably with approximately six volumes of substantially dry nitrogen gas was noted to have the greatest effect, however, reducing the dimethyl ether impurities content to only about 0.3 area percent of dimethyl ether in the final liquid volume. Filling the reaction space with increased reactant volume in order to reduce the available vapor equilibrium space resulted in amounts of less about 1.0 area percent, usually 0.8 to 0.9 area percent dimethyl ether impurities remaining.

The surprising fact that the physical displacement of the dimethyl ether gas evolved by means of the inert gas sweep will permit the dimethyl ether impurities content to be reduced to about 0.3 percent, indicates that extraordinary measures are thus required in order to remove the remaining traces of the dimethyl ether from the boron trifluoride diethyl ether complex product. The prior art clearly did not anticipate this novel finding.

The gaseous by-products of the reaction may be suitably recovered by condensation in conventional cold traps.

The following examples are intended to illustrate, but not to limit, the present invention which is set forth in broader scope in the claims that follow. Several comparative examples are interspersed among examples of the present invention to illustrate the surprisingly low dimethyl ether impurities content achieved by use of critical combination of features of the present invention.

General Experimental

GC analysis was performed on a Perkin-Elmer Model 900 Gas Chromatograph equipped with a flame ionization detector and an Auto-LAB System IVB calculating integrator. A 6 ft. (1.829 m) long $\times \frac{1}{8}$ inch (0.3175 cm) wide OD SS column packed with Tenas TM 60/80 mesh was operated isothermally at 80° C. with helium carrier gas. The integrator print peak areas and relative concentration were repeatedly compared to synthetic mixtures of known compositions.

EXAMPLE 1

Preparation of Boron Trifluoride Dimethyl Ether Complex

A 250 mL flask with a dip tube, magnetic agitator bar, riser tube and 2 cold fingers on the vent line was partially immersed in a dry ice/alcohol bath at −70° to −75° C. The primary cold finger was held at −70° to −75° C. in a dry ice/alcohol bath and the secondary cold finger at −200° C. in liquid nitrogen.

Gaseous dimethyl ether was introduced through the dip tube until 1.14 moles had been condensed out. Under gentle agitation, 1.15 moles of gaseous boron-trifluoride was slowly introduced subsurface to the condensed $(CH_3)_2O$. The cooling bath was removed and the still residue, a colorless turbid liquid, was allowed to warm to 25°–30° C. Any uncomplexed materials were purged from the system by bubbling dry nitrogen through the complex until the turbidity disappeared. Yield was 0.99 moles of material identified by nuclear magnetic resonance (NMR) as $(CH_3)_2O:BF_3$ (Boron trifluoride dimethyl either complex).

EXAMPLE 2

Dissociation of Boron Trifluoride Dimethyl Ether Complex to Boron Trifluoride Diethyl Ether Complex Large Excess of Diethyl Ether: Molar Ratio of $(C_2H_5)_2O$: $(CH_3)_2O$: $BF_3$ is 5.27:1

A 250 mL flask with thermowell, magnetic agitator bar, and a 1 inch (2.54 cm) ×5 tray vacuum jacketed distillation column with a low temperature manual flow splitter and 3 cold fingers on the vent line was immersed in a dry ice/alcohol bath at −30° C. The flow splitter condenser was maintained at −10° C., the primary cold finger at −20° C., the secondary at −70° to −75° C. and the third at −200° C. 0.38 moles of the $(CH_3)_2O:BF_3$ complex was charged to the flask. A large excess (2.0 moles) of diethyl ether was pre-chilled to −30° C. and charged to the complex. Under gentle agitation, the mixture was allowed to warm up to 25°–30° C. over a 3.5 hr. period.

Heat was applied to the flask and excess $(C_2H_5)_2O$ (diethyl ether) distilled off to a pot temperature of 58° C. The yield was 0.36 moles of $(C_2H_5)_2O:BF_3$ containing 0.1 area percent $(CH_3)_2O:BF_3$ by NMR analysis. A small amount of material trapped in the primary cold finger was identified as dimethyl ether by I.R. analysis. No boron trifluoride was detected in the third cold finger. Total recovery across the system was 95.0 weight percent based on starting materials.

This Example shows the effect of having a large excess of diethyl ether present during the reaction on the purity of the final product; the molar ratio of $(C_2H_5)_2O$ to $(CH_3)_2O:BF_3$ was 5.27:1 and the $(C_2H_5)_2O:BF_3$ contained 0.1 area percent $(CH_3)_2O:BF_3$. Apparently the extended fractional distillation of the large excess of $(C_2H_5)_2O$ forced the exchange reaction to completion and removed $(CH_3)_2O$. However, this large excess of $(C_2H_5)_2O$ necessitates large scale equipment which is difficult to maintain in a substantially dry condition, long reaction times and a careful fractional distillation to achieve this low dimethyl ether impurities level.

COMPARATIVE EXAMPLE 3

Prior Art Dissociation of Boron Trifluoride Dimethyl Ether Complex to Boron Trifluoride Diethyl Ether Complex In the test apparatus as described in Example 2, 0.58 moles of $(CH_3)_2O:BF_3$ complex was charged to the flask and chilled to −30° C. A slight excess of $(C_2H_5)_2O$ (0.72 moles) was charged to the complex and under gentle agitation the mixture was allowed to warm up to 25°–30° C. over a 3.5 hour period. Excess $(C_2H_5)_2O$ was distilled off to a pot temperature of 60° C. Yield was about 0.56 moles of $(C_2H_5)_2O:BF_3$ containing 17.0 area percent $(CH_3)_2O:BF_3$ by NMR analysis. Displaced $(CH_3)_2O$ was recovered in the secondary cold finger. Total recovery across the system was 95.5 percent.

This Comparative Example simulates the "second experiment" on page 2 of Report No. T8.10-1-3 entitled "Preparation of Diethyl Ether-Boron Trifluoride Complex" by Kenton Atwood (July 2, 1953). The results of Comparative Example 3 would be expected to be similar to said "second experiment" if the reaction were scaled up four-fold and were run in a one liter flask, and if the molar ratio of $(C_2H_5)_2O:(CH_3)_2O:BF_3$ were increased from 1.24:1 to 1.42:1. The $(CH_3)_2O:BF_3$ content in the $(C_2H_5)_2O:BF_3$ would also expected to be similar.

EXAMPLE 4

A one liter three-neck round bottom flask equipped with pressure equilibrating dropping funnel, thermometer, 18 inch (45.5 cm) long coil condenser (water cooled to a temperature between 5° and 7° C.), connected in series to a brine cooled (temperature −10° to −20° C.) partial condenser installed with separate, controllable reflux return, four cold finger traps on vent line, nitrogen inlet tube and magnetic agitator bar was immersed in an ice-water bath. The volume of this system to the top of the necks of the flask was measured as 1100 mL; under conditions of these runs, about 95% of volume of condenser was unavailable for vapor equilibration. Four cold finger traps were connected in series with vent line from partial condenser; the first cold finger at 0° (ice-water mix); the second at −20° to −22° C. (salt-ice-water mix); the third had a larger bulb and a temperature of −70° C. (dry ice-isopropanol); and the fourth at −70° C. (dry ice-isopropanol). $(CH_3)_2O:BF_3$ complex (114.6 g, 1.01 mol) was charged to the flask at a temperature of 1.8° C. and agitation was commenced. Anhydrous $(C_2H_5)_2O$ (225 g, 3.04 mol) was charged to dropping funnel and added rapidly to the stirred $(CH_3)_2O:BF_3$ complex. A water bath was supplied to the flask and heat gradually supplied over 2 hrs. as the temperature in the flask rose to 35° C. Excess $(C_2H_5)_2O$ and $(CH_3)_2O$ were distilled off. Once reaction temperature was above 36° C., little reflux was noted in the partial condenser; vigorous reflux was noted in the coil condenser. The volume ratio of vapor equilibrium region to liquid reaction mixture was about 2:1. The pot temperature was increased from 35° to 39.2° C. over 1½ hrs. to remove residual dimethyl ether. The reaction was considered complete when the pot temperature of 39.2° C. was constant for one hr. Total reaction time was 4½ hrs. The last few milliliters of distillate were not returned to the reaction to avoid addition of dissolved $(CH_3)_2O$. The liquid reaction mixture was cooled to 20°–25°, weighed (281.6 g) and sampled by IR and NMR. By NMR analysis the reaction mixture contained 98.4 area % $(C_2H_5)O:BF_3$ complex and 1.6 area % $(CH_3)_2O:BF_3$ complex. Total recovery of excess starting materials and products was 97.1% by weight.

EXAMPLES 5–7

Examples 5–7 were run as described in Example 4. The final pot temperature was between 39.5° and 39.8° C., while the volume ratio of vapor equilibrium region to liquid reaction mixture was greater than about 2:1. In each Example, the liquid reaction mixture contained less than 2 area % $(CH_3)_2O:BF_3$ complex by NMR analysis. In Examples 7 and 8, reverse addition

[(CH$_3$)$_2$O:BF$_3$ added to (C$_2$H$_5$)$_2$O] was carried out to achieve a huge excess of (C$_2$H$_5$)$_2$O at all times. No beneficial effect was observed since the 1.1 area % (CH$_3$)$_2$O:BF$_3$ (Example 7) and 1.5 area % (CH$_3$)$_2$O:BF$_3$ (Example 8) obtained in the (C$_2$H$_5$)$_2$O:BF$_3$ complex was not significantly less than 1.5–1.9 area % obtained in Examples 4–6 wherein a normal addition mode was employed. Results are summarized in Table 1 below.

TABLE 1

| | Example | | | |
|---|---|---|---|---|
| | 5 | 6 | 7* | 8* |
| (CH$_3$)$_2$O:BF$_3$ (mol) | 1.00 | 1.01 | 1.01 | 1.01 |
| (C$_2$H$_5$)$_2$O (mol) | 3.01 | 3.03 | 3.07 | 3.05 |
| Starting Temp (°C.) | 16° | 20° | 20° | 28° |
| Total Rx Time (hrs) | 4¼ | 3½ | 5¼ | 4¼ |
| Final Pot Temp (°C.) | 39.5° | 39.9° | 39.8° | 39.8° |
| Net Reactor Wt (g) | 286.7 | 284.6 | 288.7 | 286.1 |
| (CH$_3$)$_2$O in Reaction Mix | 1.9 | 1.9 | 1.1 | 1.5 |
| % Loss (wt) of Starting Mat'l and Products | 1.5 | 0.9 | 2.0 | 1.25 |

*Reverse Addition

EXAMPLE 8

This Example was run as described in Example 4 except that (CH$_3$)$_2$O:BF$_3$ (115.1 g, 1.01 mol) was added to 225.7 g, 3.05 mol of anhydrous (C$_2$H$_5$)$_2$O at 28° C. (reverse addition). The volume of the liquid reaction mixture after (CH$_3$)$_2$O:BF$_3$ addition was complete was 415 mL; volume ratio of vapor equilibrium region (585 mL) to liquid reaction mixture was 1.41:1. The coil condenser was maintained at 5° C. and the partial condenser at −10° to −12° C. The reaction pot temperature was gradually raised to 39.8° C. and maintained at 39.8° C. for 1 hr. Total reaction time was 4¼ hrs. The final volume of liquid reaction mixture was 337 mL; the volume ratio to vapor equilibrium region (793 mL) to liquid reaction (337 mL) mixture was 2.35:1. By NMR analysis, the reaction mixture in pot contained 98.5 area % (98.8 wt %) (C$_2$H$_5$)$_2$O:BF$_3$ complex and 1.5 area % (1.2 wt %) (CH$_3$)$_2$O:BF$_3$ complex. The % by weight loss of starting materials and products was 1.25% by weight.

EXAMPLE 9

This Example was run as described in Example 4 except that the final pot temperature was >40°, i.e., 40°–45° C. and the vapor equilibrium region above the liquid reaction mixture at 40°–45° C. was slowly swept with approximately 6 volumes of substantially dry N$_2$ for the final ½ hr. of reaction. To the liquid reaction mixture was added an amount of BF$_3$ sufficient to convert the residual diethyl ether into (C$_2$H$_5$)$_2$O:BF$_3$ complex. The final liquid reaction mixture (cooled to 20°–25° C.) was analyzed by NMR and GC; composition by NMR: 99.9 area % (C$_2$H$_5$)$_2$O:BF$_3$, and 0.1 area % (CH$_3$)$_2$O:BF$_3$; by GC: 99.7 volume % (C$_2$H$_5$)$_2$O:BF$_3$ and 0.3 volume % (CH$_3$)$_2$O:BF$_3$. Since NMR analysis compared the area ratio of (CH$_3$)$_2$O to (C$_2$H$_5$)$_2$O, the addition of BF$_3$ to complex residual (C$_2$H$_5$)$_2$O did not affect the analysis. Reaction conditions and results are summarized in Table 2.

EXAMPLE 10

This Example was run as described in Example 4 (normal addition). 5.73 mol (425 g) of (C$_2$H$_5$)$_2$O was added to 1.91 mol (216.6 g) of (CH$_3$)$_2$O:BF$_3$ to give a liquid reaction mixture having a volume of 820 mL at 20° C. Volume ratio of vapor equilibrium region to liquid reaction mixture was 0.34:1. After heating the liquid reaction mixture to a final pot temperature of 40° C. the final volume of liquid reaction mixture was 670 mL. The volume ratio of vapor equilibrium region to liquid reaction mixture was 0.64:1.

EXAMPLE 11

This Example was run as described in Example 4. This example demonstrated that prolonged digestion (5¼ hrs) of a liquid reaction mixture with 2 moles of (C$_2$H$_5$)$_2$O to 1 mole of (CH$_3$)$_2$O:BF$_3$ to a final pot temperature of 44° C. reduced the level of (CH$_3$)$_2$O:BF$_3$ to 0.9 area % (NMR) (0.8 weight % by GC).

TABLE 2

| | Example | | |
|---|---|---|---|
| | 9 | 10 | 11 |
| (CH$_3$)$_2$O:BF$_3$ (mol) | 3.01 | 5.73 | 5.81 |
| (C$_2$H$_5$)$_2$O (mol) | 1.01 | 1.91 | 2.89 |
| Mole Ratio (C$_2$H$_5$)$_2$O:(CH$_3$)$_2$O:BF$_3$ | 3:1 | 3:1 | 2:1 |
| Starting Temp (°C.) | 19.2 | 15.5 | 15 |
| Time to 35° C. (hrs) | 1 | 2 | 1¾ |
| Total Rx Time (hrs) | 4¼ | 5¼ | 5¼ |
| Final Pot Temp (°C.) | >40 | 40 | 44 |
| Net Wt Final Reaction Mix (g) | 279.2 | 538.8 | 610.7 |
| (CH$_3$)$_2$O compared to (C$_2$H$_5$)$_2$O in Reaction Mix | NMR 0.1 area % | 0.9 | 0.9 |
| | GC 0.3 vol. % | — | 0.8 |
| % Loss of Starting Mat'l and Products | 2.7% | 1% | 0.2% |
| Variation | N$_2$ sweep for ½ hr. | Large Batch | 2:1 and Large Batch |

EXAMPLE 12

This Example is run as described in Example 10. The molar ratio of (C$_2$H$_5$)$_2$O to (CH$_3$)$_2$O:BF$_3$ is 3:1. The total reaction time is 5¼ hrs. and final pot temperature, 40°–45° C., is maintained for at least one hr. During the last ½ hr., the vapor equilibrium region is swept with 6 volumes of substantially dry N$_2$. The percent of (CH$_3$)$_2$O:BF$_3$ is as in Example 9.

COMPARATIVE EXAMPLE 13

This Example was run exactly as described in Example 4 except that the final pot temperature was 36° C. The volume ratio of the vapor equilibration region to liquid reaction mixture was more than about 2:1 when temperature of pot was 35°–36° C. By NMR there was 5 area % (CH$_3$)$_2$O:BF$_3$ in the final liquid reaction mixture.

EXAMPLES 14–16

In the following examples, the process of Example 4 is repeated in the same apparatus excepting that the dialkyl ether reactant is varied as indicated in the following table. In all the examples good yields of the indicated products substantially free of boron trifluoride dimethyl ether complex are obtained. The molar ratio of R$_1$R$_2$O:(CH$_3$)$_2$O:BF$_3$ is 3:1, the final pot temperature of 40°–45° C. is maintained for at least one hr.

TABLE 3

| Example | Dialkyl Ether R$_1$R$_2$O | Product R$_1$R$_2$O:BF$_3$ |
|---|---|---|
| 14 | R$_1$ = n-hexyl | R$_1$ = n-hexyl |

TABLE 3-continued

| Example | Dialkyl Ether $R_1R_2O$ | Product $R_1R_2O:BF_3$ |
|---|---|---|
| 15 | $R_2$ = n-hexyl<br>$R_1$ = methyl | $R_2$ = n-hexyl<br>$R_1$ = methyl |
| 16 | $R_2$ = n-hexyl<br>$R_1$ = isopropyl<br>$R_2$ = ethyl | $R_2$ = n-hexyl<br>$R_1$ = isopropyl<br>$R_2$ = ethyl |

The volume ratio of vapor equilibrium region to liquid reaction mixture is 0.8:1.

EXAMPLES 17–19

The process of Examples 14–16 is repeated excepting that the vapor equilibrium region is swept with substantially dry $N_2$ for at least the final ½ hr. of reaction.

EXAMPLES 20–22

The process of Examples 14–16 is repeated excepting that the molar ratio is 2:1 and the volume ratio is 0.5:1.

EXAMPLES 23–25

The process of Examples 20–22 is repeated excepting that the vapor equilibrium region is swept with substantially dry $N_2$ gas for the last ½ hr. of reaction.

We claim:

1. A process for the conversion of boron trifluoride-dimethyl ether complex into boron trifluoride-dialkyl ether complex substantially free of dimethyl ether impurities, which comprises:
   (a) contacting the boron trifluoride diemthyl ether complex essentially free of boron trifluoride, in the liquid phase, with an effective amount of dialkyl ether wherein at least one alkyl group contains at least two carbon atoms in a reaction zone to form a liquid reaction mixture comprising boron trifluoride dialkyl ether complex and residual dimethyl ether and excess diethyl ether;
   (b) restricting vapor equilibrium region above the liquid reaction mixture in the reaction zone, while heating the liquid reaction mixture for a time and at a temperature sufficient to remove the residual dimethyl ether and to form boron trifluoride dialkyl ether complex substantially free of dimethyl ether impurities; and
   (c) recovering boron trifluoride dialkyl ether complex substantially free of dimethyl ether impurities.

2. The process as described in claim 1 which further comprises sweeping the vapor equilibrium region above the liquid reaction mixture in step (b) with substantially dry inert gas for a time sufficient to remove the residual dimethyl ether.

3. The process as described in claim 1 or 2 wherein the dialkyl ether has a formula $R_1R_2O$ wherein $R_1$ is an acyclic alkyl group of two to six carbon atoms and wherein $R_2$ is acyclic alkyl group of one to six carbon atoms.

4. The process as described in claim 1 or 2 wherein in step (a) a temperature in the range of about $-30°$ to about 35° C. is maintained.

5. The process as described in claim 1 or 2 wherein in step (b) a temperature in the range of about 35° to no more than about 50° C. is maintained.

6. The process as described in claim 1 or 2 wherein in step (a) a molar ratio of boron trifluoride dimethyl ether complex to dialkyl ether is in the range of about 1:1 to about 1:3.5.

7. The process as described in claim 6 wherein said molar ratio is in the range of about 1:2 to about 1:3.

8. The process as described in claim 1 or 2 wherein in step (b) volume ratio of said vapor equilibrium region to liquid reaction mixture is in the range of about 0.3:1 to about 3:1.

9. The process as described in claim 8 wherein said volume ratio is in the range of about 0:5:1 to about 0.8:1 and said molar ratio is in the range of about 1:2 to 1:3.

10. A process for the conversion of boron triflouride dimethyl ether complex into boron trifluoride diethyl ether complex substantially free of dimethyl ether impurities, which comprises:
    (a) contacting about one mole of boron trifluoride dimethyl ether complex substantially free of boron trifluoride, in the liquid phase, with about 2 to about 3 moles of diethyl ether, in a reaction zone at a temperature of about $-30°$ C. to about 35° C. to form a liquid reaction mixture comprising boron trifluoride diethyl ether complex, residual dimethyl ether, and excess diethyl ether;
    (b) restricting vapor equilibrium region above the liquid reaction mixture in the reaction zone, while heating the liquid reaction mixture at a temperature from about 35° C. to no more than about 45° C. for a time sufficient to remove the residual dimethyl ether and excess diethyl ether and to form boron trifluoride diethyl ether complex substantially free of dimethyl ether impurities, the volume ratio of said vapor region to said liquid reaction mixture being about 0.5:1 to about 0.8:1; and
    (c) recovering boron trifluoride diethyl ether complex substantially free of dimethyl ether impurities.

11. The process as described in claim 10 which further comprises sweeping the restricted vapor equilibrium region above the liquid reaction mixture in step (b) with substantially dry nitrogen gas for a time sufficient to remove the residual dimethyl ether.

* * * * *